United States Patent [19]

Yohji et al.

[11] 4,395,562
[45] Jul. 26, 1983

[54] VINYLIDENE-SILICON-COMPOUND AND A PROCESS FOR ITS PRODUCTION

[75] Inventors: Terui Yohji, Chibashi; Koga Isao, Sakurashi; Ohtake Nobumasa, Yokohamashi, all of Japan

[73] Assignee: Chisso Corporation, Osaka, Japan

[21] Appl. No.: 366,421

[22] Filed: Apr. 7, 1982

[30] Foreign Application Priority Data

Apr. 15, 1981 [JP] Japan .................................. 56-56507

[51] Int. Cl.$^3$ ............................ C07F 7/08; C07F 7/18
[52] U.S. Cl. ..................................... 556/431; 556/435
[58] Field of Search ......................................... 556/431

[56] References Cited

U.S. PATENT DOCUMENTS

| 2,561,429 | 7/1951 | Sveda .............................. 556/431 X |
| 2,588,083 | 3/1952 | Burkhard et al. ............... 556/431 X |
| 3,322,807 | 5/1967 | Johnson ............................. 556/431 |
| 3,470,226 | 9/1969 | Plumb et al. ...................... 556/431 |
| 3,666,783 | 5/1972 | LeFort ............................... 556/431 |

OTHER PUBLICATIONS

Journal of Organometallic Chemistry, 199 (1980), 43–47, 185–193, H. Matsumoto et al.

*Primary Examiner*—Paul F. Shaver

*Attorney, Agent, or Firm*—Wenderoth, Lind & Ponack

[57] ABSTRACT

A novel silicone compound having a group such as methoxy group, which can be bonded to an inorganic substance and a vinylidene group and being useful as a silane coupling agent. The compound has the following general formula

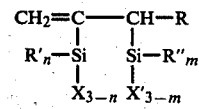

where R is an alkyl group of 1 to 7 carbon atoms or a hydrogen atom; R' and R" respectively represent an alkyl group of 1 to 7 carbon atoms; X and X' respectively represent a chlorine atom or an alkoxy group of 1 to 4 carbon atoms; and n and m respectively represent an integer of 0 to 3.

The compound is prepared by reacting an alkyl allene represented by the general formula $H_2C=C=CHR$ with a disilane represented by the general formula $R'_n X_{3-n} Si_2 R''_m X'_{3-n}$ (where R, R', R", X, X', n and m are as defined above) in the presence of a phosphine complex of a transition metal.

4 Claims, 6 Drawing Figures

VINYLIDENE-SILICON-COMPOUND AND A PROCESS FOR ITS PRODUCTION

BACKGROUND OF THE INVENTION

(1) Field of the Invention

The present invention relates to a novel organic silicone compound and a process for its production.

(2) Description of the Prior Art

Silicone compound having a functional group such as a vinyl group or an amino group reactive with an organic material or a functional group such as a methoxy group or a chlorine atom which can be bonded to an inorganic material are commonly used as silane coupling agents for improvement of the properties of various industrial products. However, the recent development of industrial techniques demands a development of a further novel organic silicone compounds.

SUMMARY OF THE INVENTION

The present invention provides a novel organic silicone compound having a vinylidene group and two silicone atoms, which has not been known heretofore, and a process for preparing it.

Namely, according to the present invention, there is provided a vinylidene silicone compound represented by the general formula

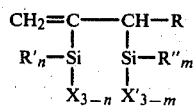

where R is an alkyl group of 1 to 7 carbon atoms or a hydrogen atom; each of R' and R" represents an alkyl group of 1 to 7 carbon atoms; each of X and X' represents a chlorine atom or an alkoxy group of 1 to 4 carbon atoms; each of n and m represents an integer of 0 to 3. According to the present invention, there is provided also a process for preparing the above mentioned vinylidene silicone compound, which comprises reacting an alkyl allene represented by the general formula $H_2C=C=CHR$ (where R is as defined above) with a disilane represented by the general formula $R'_nX_{3-n}Si_2R''_mX'_{3-m}$ (where R', R", X, X', n and m are as defined above) in the presence of a phosphine complex of a transition metal such as $Pd(PPh_3)_4$, $PdCl_2(PPh_3)_2$, $Pt(PPh_3)_4$, $PtCl_2(PPh_3)_2$, $RhCl(PPh_3)_3$, $NiCl_2(PPh_3)_2$ or $RuCl_2(PPh_3)_3$.

DETAILED DESCRIPTION OF THE INVENTION AND THE PREFERRED EMBODIMENTS

Figure 1:
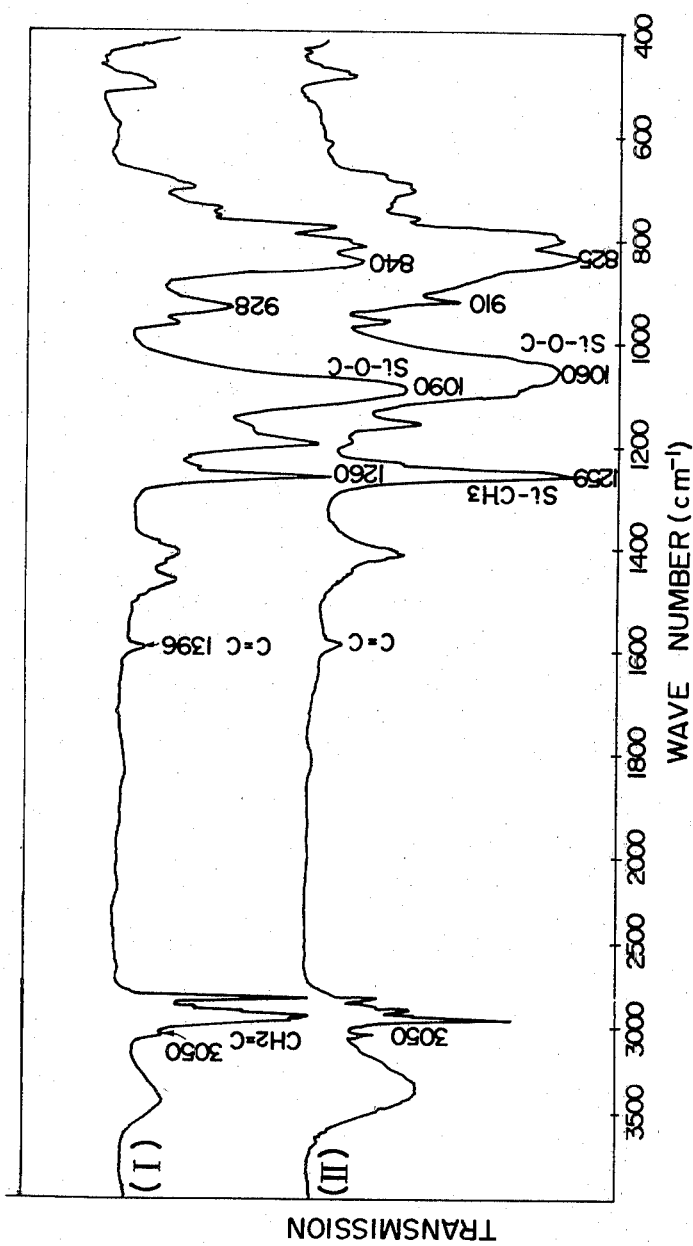
FIGS. 1 to 6 shows infrared spectra of vinylidene silicone compounds obtained by the Examples.
Figure 2:
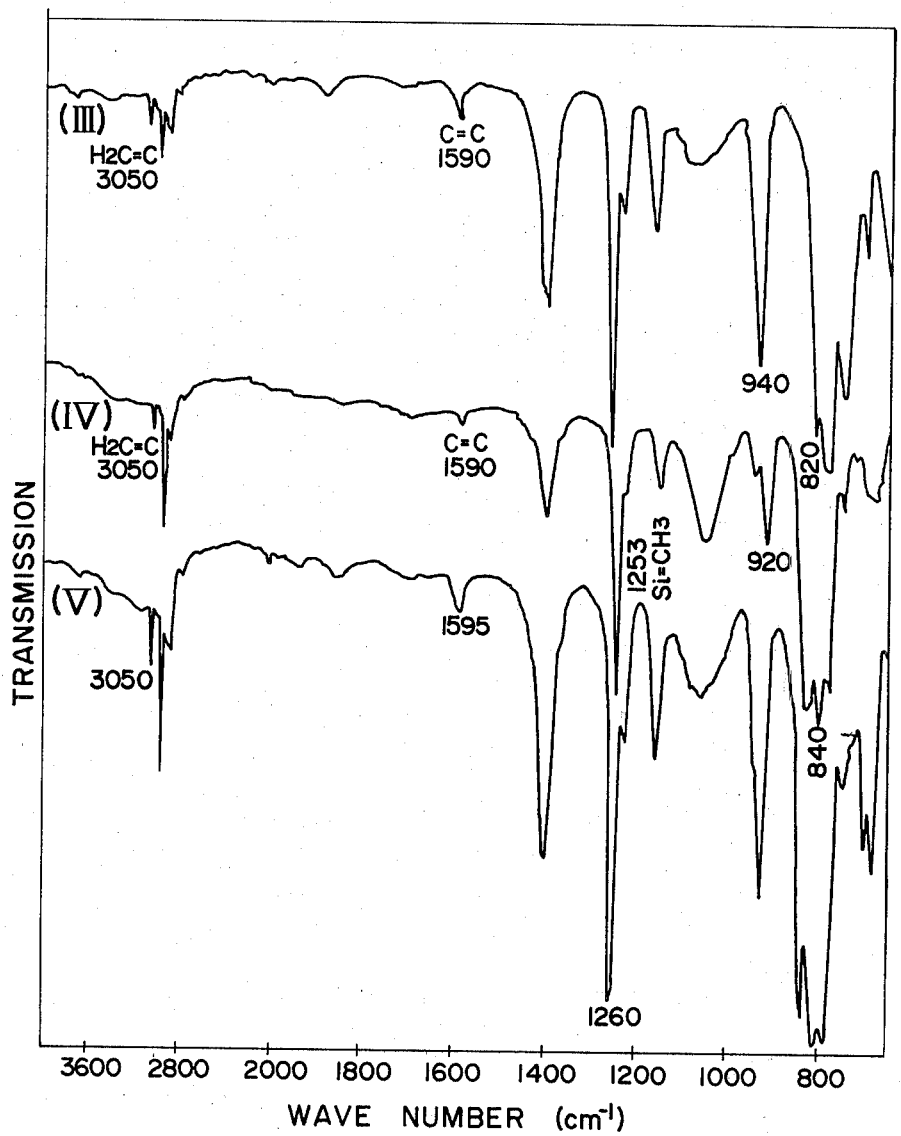
Figure 3:
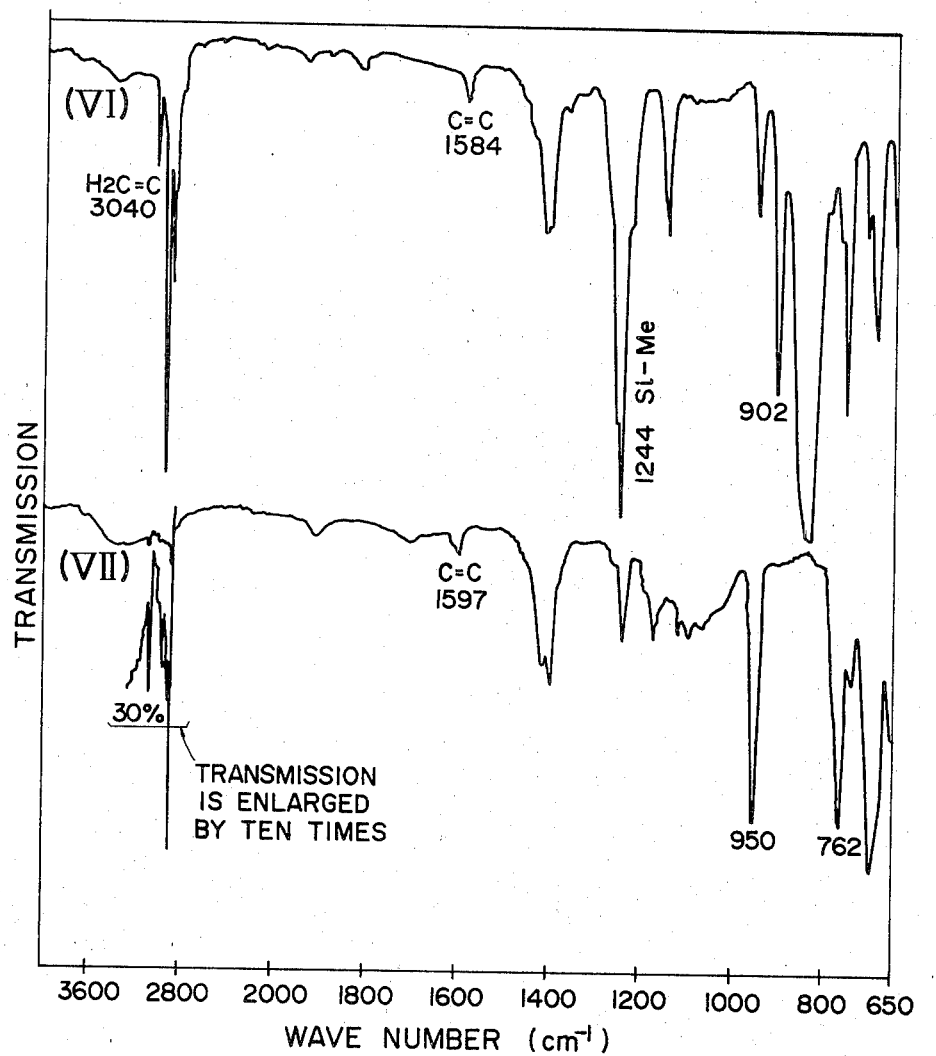
Figure 4:
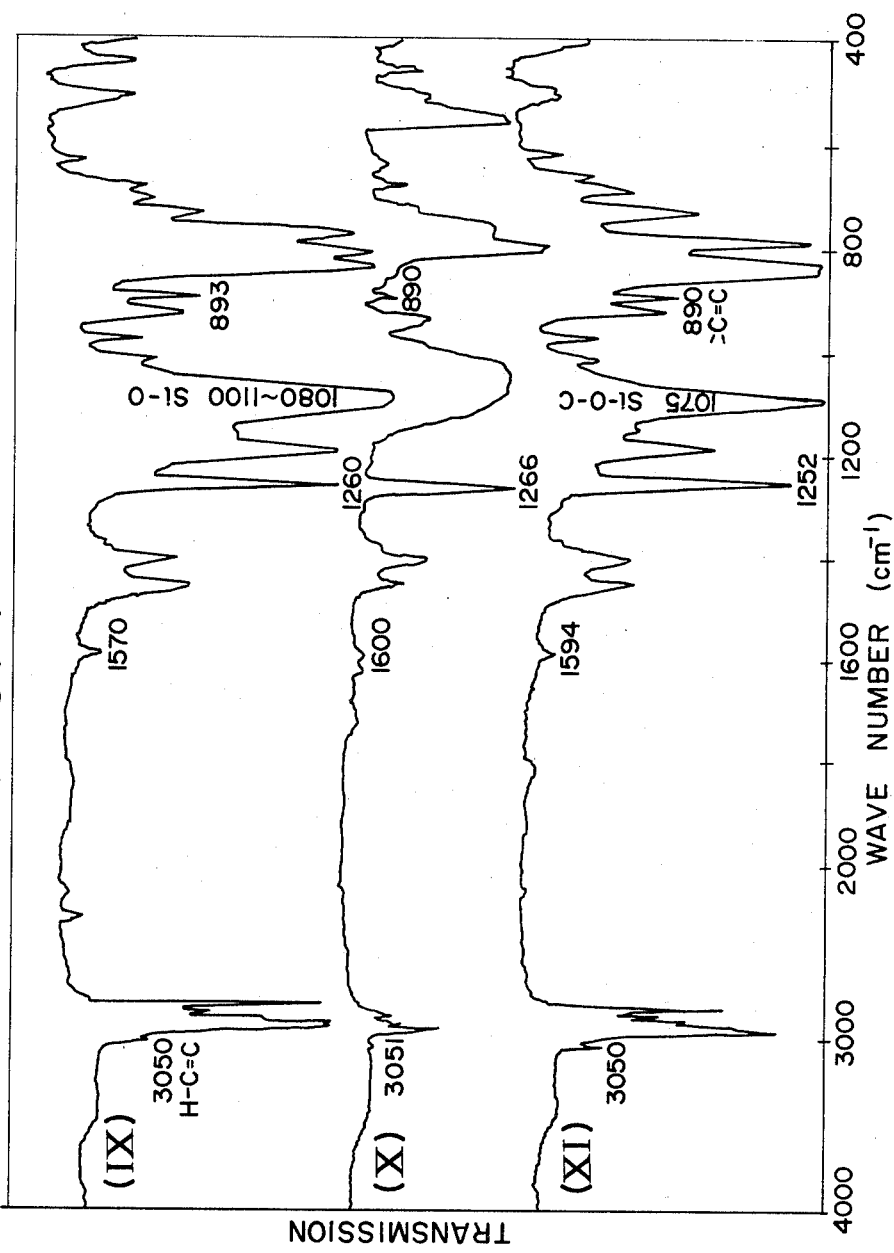
Figure 5:
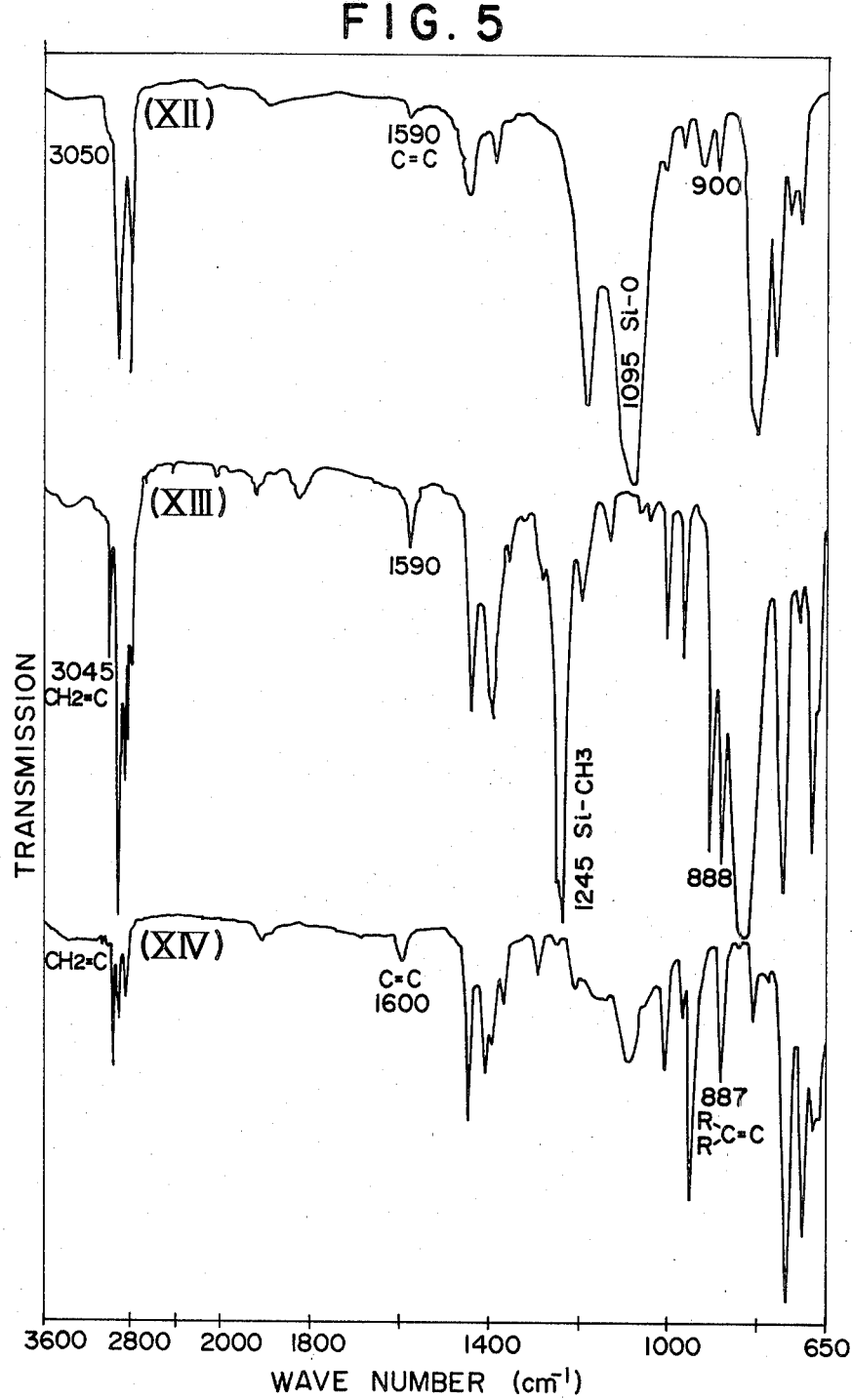
Figure 6:
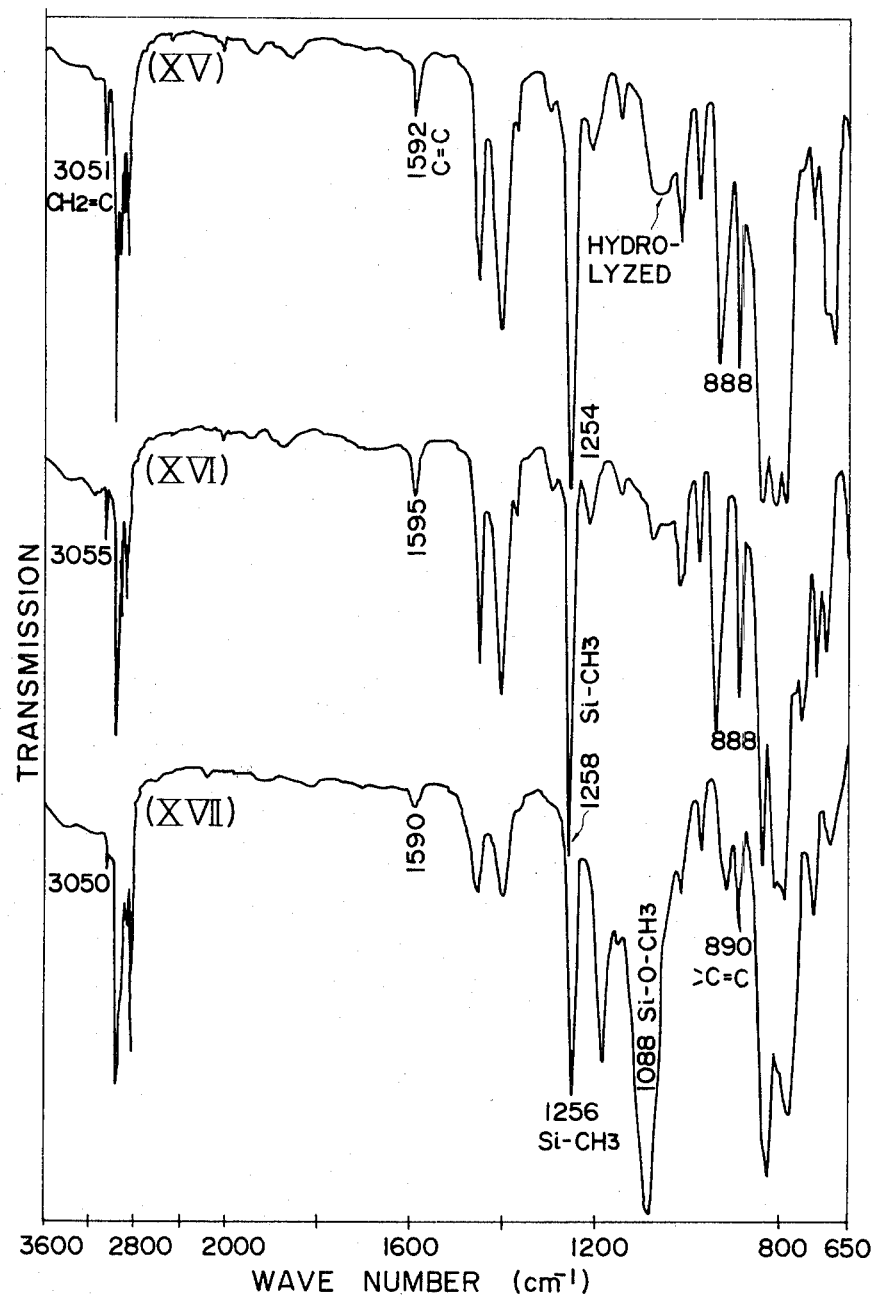

As specific examples of the vinylidene silicone compounds of the present invention, there may be mentioned 2,3-bis(trimethylsilyl)propene-1; 2,3-bis(methyldimethoxysilyl)propene-1; 2,3-bis(methoxydimethylsilyl)propene-1; 2,3-bis(trimethoxysilyl)propene-1; 2,3-bis(chlorodimethylsilyl)propene-1; 2,3-bis(dichloromethylsilyl)propene-1, 2,3-bis(trichlorosilyl)propene-1; 2-methoxydimethylsilyl-3-trimethylsilyl-propene-1; 2-dimethoxymethylsilyl-3-methoxydimethylsilyl-propene-1; 2-trimethoxysilyl-3-methyldimethoxysilyl-propene-1; 2-chlorodimethylsilyl-3-dichloromethylsilyl-propene-1; 2-chlorodimethyl-3-dichloromethylsilylpropene-1; 2,3-bis(trimethylsilyl)butene-1; 2,3-bis(methyldimethoxysilyl)butene-1; 2,3-bis(methoxydimethylsilyl)butene-1; 2,3-bis(trimethoxysilyl)butene-1; 2,3-bis(chlorodimethylsilyl)butene-1; 2,3-bis(dichloromethylsilyl)butene-1; 2,3-bis(trichlorosilyl)propene-1; 2-methoxydimethylsilyl-3-trimethylsilyl-butene-1; 2-dimethoxymethylsilyl-3-methoxydimethylsilyl-butene-1; 2-trimethoxysilyl-3-methyldimethoxysilyl-butene-1; 2-trimethylsilyl-3-chlorodimethyl-butene-1 and; 2-chlorodimethylsilyl-3-dichloromethylsilyl-butene-1.

The process of the present invention comprises reacting the alkyl allene with the disilane in the presence of the phosphine complex of a transition metal. The reaction temperature may be from 50° to 200° C. However, it is preferably from 80° to 150° C. The reaction time may be from one to 24 hours. The ratio of the alkyl allene and the disilane may be equi-molar ratio. However, it is preferred that the alkyl allene is used in an excess amount. The amount of the phosphine complex of the transition metal is from 0.01 to 5.0 molar % based on the disilane. However, it is preferably from 0.1 to 1.0 molar %.

The alkyl allene to be used in the present invention is a compound represented by the general formula $H_2C=C=CHR$ (where R is an alkyl group of 1 to 7 carbon atoms or a hydrogen atom). As the specific compounds, there may be mentioned allene, methyl allene (1,2-butadiene), ethyl allene (1,2-pendadiene), propyl allene (1,2-hexadiene), isopropyl allene, butyl allene (1,2-heptadiene), pentyl allene (1,2-octadiene) and t-butyl allene.

The disilane to be used in the present invention is a compound represented by the general formula $R'_nX_{3-n}Si_2R''_mX'_{3-m}$ (where each of R' and R" is an alkyl group of 1 to 7 carbon atoms; each of X and X' is a chlorine atom or an alkoxy group of 1 to 4 carbon atoms; and each of n and m is an integer of 0 to 3). As the specific compounds, there may be mentioned hexamethyldisilane, hexaethyldisilane, hexamethoxydisilane, hexachlorodisilane, dimethyltetramethoxydisilane, diethyl-tetramethoxydisilane, dimethoxy-tetramethyldisilane, dimethyl-tetrachlorodisilane, dichloro-tetramethyldisilane, trimethyl-trichlorodisilane, trimethoxytrimethydisilane, monochloro-pentamethyldisilane, monomethoxypentamethyldisilane, monomethylpentachlorodisilane, monomethyl-pentamethoxydisilane, hexaethoxydisilane, diethyl-tetramethoxydisilane, diethyltetrachlorodisilane, dichloro-tetraethyldisilane, triethyl-trichlorodisilane, trimethoxy-triethyldisilane, monochloro-pentaethyldisilane, monomethoxy-pentaethyldisilane, monoethyl-pentachlorodisilane or other ethoxy, propoxy or isopropoxy silanes corresponding to the above.

The feature of the compound of the present invention is that it has in its molecule a vinylsilane group ($CH_2=C-Si\equiv$) and a allylsilane group

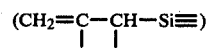

and the silicon may simultaneously have various alkyl groups or/and a chlorine atom, a methoxy group, an ethoxy group, etc. Thus, this compound has properties suitable for a wide range of applications for organic chemical reagents or organic synthetic intermediates, reforming agents for various silicones or silane coupling agents.

If the reaction in the process of the present invention is conducted by a reactor equipped with a pressure resistant gauge, a time point when the change (i.e. a decrease) in the internal pressure ceases, can be taken as the completion of the reaction, whereby the reaction time can be shortened. Further, a commercial 1,2-butadiene contains butene-2 as the major impurity, and even when it is used per se, only 1,2-butadiene is double silylated.

Now, the present invention will be described with reference to Examples.

EXAMPLES 1 TO 10 after referred to simply as NMR) and the structure of the compounds thereby obtained are shown in Table 3. Further, the infra-red spectra (hereinafter referred to simply as IR) are shown in the Figures.

EXAMPLES 11 TO 23

The operation was carried out in a manner similar to Examples 1 to 10 except that the allene was replaced by 1,2-butadiene and the molar ratio was changed. The conditions and the results thereby obtained are shown in Table 4. The physical values of the compounds thereby obtained are shown in Table 5, and the NMR data and the structures of the compounds thereby obtained are shown in Table 6. The IR is shown in Figures.

TABLE 1

| | | Reaction conditions[*1] | | | Conversion rates of the disilanes [%] | Products | | Reference symbols of the products |
|---|---|---|---|---|---|---|---|---|
| | | Temperatures [°C.] | Time [hr] | solvents | | Yields | | |
| Examples | Disilanes $R'_nX_{3-n}Si_2R''_mX'_{3-n}$ | | | | | [GLC %] | Isolation [%] | |
| 1 | Me(OMe)₂Si₂Me(OMe″)₂ | 120 | 6 | None | 82 | 49 | 24 | } [I] |
| 2 | " | 120 | 20 | " | 99 | 50 | 40 | |
| 3 | Me₂OMeSi₂Me₂OMe | 100 | 16 | " | 84 | 48 | 32 | } [II] |
| 4 | " | 120 | 20 | " | 93 | 50 | 37 | |
| 5 | MeCl₂Si₂MeCl₂ | 120 | 15 | " | 100 | 85 | 67 | [III] |
| 6 | Me₂ClSi₂Me₂Cl | " | " | " | 100 | 93 | 68 | [IV] |
| 7 | Me₂ClSi₂MeCl₂ | " | " | " | 100 | 77 | 53 | [V] |
| 8 | Me₃Si₂Me₃ | " | 20 | PhH | 30 | 29 | — | [VI] |
| 9 | Cl₃Si₂Cl₃ | 175 | 24 | C₆H₃Me₃ | 51 | 43 | — | [VII] |
| 10 | Me(OMe)₂Si₂Me₂(OMe) | 120 | 20 | None | 100 | 64 | 55 | [VIII] |

Notes:
Me represents CH₃ and Ph represents C₆H₅.
[*1] Disilane/allene/Pd(PPh₃)₄ = 10/20/0.1 (m mol)

10 m mol of a disilane as shown in Table 1 and 0.1 m mol of Pd(PPh₃)₄ catalyst were fed to a pressure resistant reactor made of stainless steel, having a capacity of from 100 to 200 ml and containing a magnetic stirrer, and after degasification, 20 ml of liquefied allene was added, and the reaction was carried out in an oil bath at a temperature as shown in Table 1 while stirring for a period of time as shown in Table 1. After the reaction, the reaction solution was analyzed by gaschromatography to measure the conversion rate of the disilane and the yield of the intended organic silicone compound (based on the disilane). The results thereby obtained are shown in Table 1. Further, the physical values of the compounds thereby obtained are shown in Table 2, and the data of nuclear magnetic resonance spectra (herein-

TABLE 2

| | Elemental analysis values (%)[*] | | Boiling points [°C./mmHg] | $n_D^{25}$ | Molecular formulas |
|---|---|---|---|---|---|
| | H | C | | | |
| [I] | 8.56(8.86) | 42.87(43.16) | 102/20 | 1.4264 | C₉H₂₂O₄Si₂ |
| [II] | 10.13(10.15) | 49.29(49.49) | 96/25 | 1.4329 | C₉H₂₂O₂Si₂ |
| [III] | 3.63(3.76) | 22.43(22.40) | 105/30 | 1.4780 | C₅H₁₀Cl₄Si₂ |
| [IV] | 6.93(6.76) | 37.43(37.46) | 103/42 | 1.4631 | C₇H₁₆Cl₂Si₂ |
| [V] | 5.06(5.29) | 28.99(29.09) | 100/35 | 1.4700 | C₆H₁₃Cl₃Si₂ |
| [VI] | 11.88(11.89) | 58.31(57.98) | 63/60 | 1.4384 | C₉H₂₂Si₂ |
| [VII] | 1.67(1.30) | 11.87(11.66) | 75/12 | 1.4868 | C₃H₄Cl₆Si₂ |
| [VIII] | 9.17(9.46) | 45.75(46.11) | 70/5 | 1.4286 | C₉H₂₂O₃Si₂ |

[*] The value in the bracket ( ) is a theoretical value.

TABLE 3

| Structural formulas | | δ (ppm) | Measured values | Theoretical values |
|---|---|---|---|---|
| [I] CH₃ <br> \|a <br> H₂C=C—CH₂—Si(OCH₃)₂ <br> d \| b    c <br> Si(OCH₃)₂ <br> \|   c <br> CH₃ <br> a' | a,a' <br> b <br> c <br> d | 0.05,0.13(2s) <br> 1.64(s) <br> 3.47(s) <br> 5.25 ~ 5.72(m) | 6.4 <br> 1.8 <br> 12 <br> 1.8 | 6 <br> 2 <br> 12 <br> 2 |

TABLE 3-continued

| Structural formulas | | δ (ppm) | Measured values | Theoretical values |
|---|---|---|---|---|
| [II] H$_2$C=C—CH$_2$—Si(CH$_3$)$_2$OCH$_3$ with SiOCH$_3$(CH$_3$)$_2$ branch (a=OCH$_3$/SiCH$_3$, b=CH$_2$, c=OCH$_3$, d=CH) | a<br>b<br>c<br>d | 0.08,0.15(2s)<br>1.67(s)<br>3.40(s)<br>5.13 ~ 5.59(m) | 12<br>1.9<br>5.9<br>1.9 | 12<br>2<br>6<br>2 |
| [III] H$_2$C=C—CH$_2$—SiCH$_3$Cl$_2$ with Cl$_2$SiCH$_3$ branch | a$_1$<br>a$_2$<br>b<br>c | 0.83(s)<br>0.89(s)<br>2.34(s)<br>5.63 ~ 6.18 | }6.1<br>-2<br>2 | 6<br>2<br>2 |
| [IV] CH$_2$=C—CH$_2$—SiCl(CH$_3$)$_2$ with SiCl(CH$_3$)$_2$ branch | a<br>b<br>c | 0.45(s),0.51(s)<br>1.99(s)<br>5.39-5.89(m) | 12.0<br>2.1<br>2 | 12<br>2<br>2 |
| [V] CH$_2$=C—CH$_2$SiCH$_3$Cl$_2$ with Si(CH$_3$)$_2$Cl branch | a<br>b<br>c<br>d | 0.51(s)<br>0.80(s)<br>2.26(s)<br>5.76(m) | 6.0<br>2.9<br>2.0<br>2 | 6<br>3<br>2<br>2 |
| [VI] CH$_2$=C—CH$_2$—Si(CH$_3$)$_3$ with Si(CH$_3$)$_3$ branch | a<br>b<br>c | 0.00(s),0.06(s)<br>1.58(s)<br>5.08 ~ 5.45(m) | 18<br>2.0<br>2.0 | 18<br>2<br>2 |
| [VII] CH$_2$=C—CH$_2$—SiCl$_3$ with SiCl$_3$ branch | a<br>b | 2.63(s)<br>6.10 ~ 6.40(m) | 20.5<br>2 | 2<br>2 |
| [VIII] CH$_2$=C—CH$_2$SiMe$_2$(OMe) with SiMe(OMe)$_2$ branch | a<br>a<br>c<br>c<br>e<br>f | 0.12<br>0.02<br>3.37<br>3.47<br>1.63<br>5.17 ~ 5.70(m) | 5.8<br>3.2<br>3.0<br>6.0<br>2.0<br>2 | 6<br>3<br>3<br>6<br>2<br>2 |

TABLE 4

| Examples | Disilanes R'$_n$X$_{3-n}$Si$_2$R''$_m$X'$_{3-m}$ | Conditions*[2] Temperatures [°C.] | Time [hr] | Conversion rates of the disilanes [%] | Yield GLC % | Isolation [%] | Reference symbols of the products |
|---|---|---|---|---|---|---|---|
| 11 | Me(OMe)$_2$Si$_2$Me(OMe)$_2$ | 120 | 15 | 100 | 88 | 86 | } [IX] |
| 12 | " | 100 | 16 | 100 | 92 | 80 | |
| 13 | MeCl$_2$Si$_2$MeCl$_2$ | 100 | 3 | 100 | 85 | 41 | [X] |
| 14 | Me$_2$OMeSi$_2$Me$_2$OMe | 120 | 5 | 93 | 91 | 80 | } [XI] |
| 15 | " | 120 | 15 | 100 | 97 | 88 | |
| 16 | (OMe)$_3$Si$_2$(OMe)$_3$ | 100 | 15 | 98 | 64 | 42 | [XII] |
| 17 | Me$_3$Si$_2$Me$_3$ | 120 | 15 | 100 | 83 | 73 | } [XIII] |
| 18 | " | 150 | 24 | 76 | 84 | 66 | |
| 19 | Cl$_3$Si$_2$Cl$_3$ | 120 | 5 | 98 | 84 | 48 | [XIV] |
| 20 | Me$_2$ClSi$_2$Me$_2$Cl | 100 | 5 | 77 | 58 | 49 | } [XV] |
| 21 | " | 130 | 15 | 98 | 84 | 75 | |
| 22 | Me$_2$ClSi$_2$MeCl$_2$ | 100 | 15 | 100 | 81 | 59 | [XVI] |
| 23 | Me$_2$(OMe)Si$_2$Me(OMe)$_2$ | 120 | 15 | 100 | 57 | | [XVII] |

*[2]Disilane/1,2-butadiene/Pd(PPh$_3$)$_4$ = 10/10/0.1 (m mol)

TABLE 5

| | Elemental analysis values (%)* | | Molecular formulas | Boiling points [°C./mmHg] | $n_D^{25}$ |
|---|---|---|---|---|---|
| | H | C | | | |
| [IX] | 8.88(9.15) | 45.38(45.42) | $C_{10}H_{24}O_4Si_2$ | 105 ~ 107/27 | 1.4311 |
| [X] | 4.03(4.29) | 25.80(25.54) | $C_6H_{12}Cl_4Si_2$ | 89/18 | 1.4801 |
| [XI] | 10.28(10.41) | 51.74(51.67) | $C_{10}H_{24}O_2Si_2$ | 103/30 | 1.4395 |
| [XII] | 7.79(8.16) | 40.49(40.51) | $C_{10}H_{24}O_6Si_2$ | 107/30 | 1.4236 |
| [XIII] | 11.92(12.07) | 60.32(59.91) | $C_{10}H_{24}Si_2$ | 67 ~ 67.5/30 | 1.4236 |
| | | | | | 1.4442 |
| [XIV] | 2.08(1.87) | 14.93(14.88) | $C_4H_6Si_2Cl_6$ | 106 ~ 109/28 | 1.4881 |
| [XV] | 7.51(7.52) | 39.87(39.82) | $C_8H_{18}Si_2Cl_2$ | 100 ~ 103/30 | 1.4660 |
| [XVI] | 5.53(5.78) | 31.96(32.12) | $C_7H_{15}Si_2Cl_3$ | 99/30 | 1.4755** |
| [XVII] | 9.45(9.74) | 48.19(48.34) | $C_{10}H_{24}O_3Si_2$ | 104 ~ 105/30 | 1.4383** |

*The value in the bracket ( ) is a theoretical value.
**20° C.

TABLE 6

| | Structural formulas | δ (ppm) | Measured values | Theoretical values |
|---|---|---|---|---|
| [IX] | $H_3C$—Si(OCH$_3$)$_2$ (e, b)<br>$H_2C$=C—CH—CH$_3$ (a, c, d)<br>$H_3C$—Si(OCH$_3$)$_2$ (e, b) | a 5.7 ~ 5.4<br>b 3.5<br>c 2.1 ~ 1.7<br>d 1.20 ~ 0.97<br>e 0 ~ 0.2 | 2.0<br>12.0<br>1.0<br>3.0<br>6 | 2<br>12<br>1<br>3<br>6 |
| [X] | $H_3CSiCl_2$ (a)<br>$H_2C$=C—CH—CH$_3$ (e, d, c)<br>$H_3CSiCl_2$ (a) | a 0.77(s)<br>a 0.89(s)<br>c 1.3(d)<br>d 2.32(g)<br>e 5.90(s), 6.07(s) | }6.4<br>3.2<br>1.2<br>2 | 6<br>3<br>1<br>2 |
| [XI] | $H_3COSi(CH_3)_2$ (e, a)<br>$H_2C$=C—CH—CH$_3$ (f, d, c)<br>$H_3COSi(CH_3)_2$ (e, a) | a 0<br>a 0.1<br>c 1.1<br>d 1.8<br>e 3.38<br>f 5.47 | }11.8<br>3<br>1.1<br>5.7<br>1.8 | 12<br>3<br>1<br>6<br>2 |
| [XII] | Si(OCH$_3$)$_3$ (c)<br>$H_2C$=C—CH—CH$_3$ (d, b, a)<br>Si(OCH$_3$)$_3$ (c) | a 1.15(d)<br>b 1.88(g)<br>c 3.54(s)<br>d 5.65(d) | 3<br>1.1<br>18.4<br>1.7 | 3<br>1<br>18<br>2 |
| [XIII] | Si(CH$_3$)$_3$ (a)<br>$H_2C$=C—CH—CH$_3$ (e, d, c)<br>Si(CH$_3$)$_3$ (a) | a 0.0 (s)<br>a 0.07(s)<br>c 1.13(d)<br>d 1.67(m)<br>e 5.40(d) | }17.6<br>3<br>1<br>1.8 | 18<br>3<br>1<br>2 |
| [XIV] | SiCl$_3$<br>$H_2C$=C—CH—CH$_3$ (c, b, a)<br>SiCl$_3$ | a 1.50(d)<br>b 2.63(g)<br>c 6.29(d) | 2.92<br>1.23<br>2.0 | 3<br>1<br>2 |
| [XV] | ClSi(CH$_3$)$_2$ (a)<br>$H_2C$=C—CH—CH$_3$ (e, d, c)<br>ClSi(CH$_3$)$_2$ (b) | a 0.36(s)<br>b 0.43(s)<br>c 1.50(d)<br>d 2.23(g)<br>e 5.47(d), 5.63(d) | }12.0<br>3.4<br>1.2<br>2.0 | 12<br>3<br>1<br>2 |

TABLE 6-continued

| Structural formulas | δ (ppm) | Measured values | Theoretical values |
|---|---|---|---|
| [XVI] H$_2$C=C—CH—SiCl$_2$(CH$_3$) with CH$_3$ (c) above CH, and Si(CH$_3$)$_2$Cl (b) below C; labels e, d, a | a 0.80(s)<br>b 0.55(s)<br>c 1.37(d)<br>d 2.31(q)<br>e 5.76(s), 6.01(s) | 3.0<br>6.0<br>3.0<br>1.15<br>2 | 3<br>6<br>3<br>1<br>2 |
| [XVII] CH$_2$=C—CH—Si(CH$_3$)$_2$(OCH$_3$) with CH$_3$ (e) above CH, and Si(CH$_3$)(OCH$_3$)$_2$ (b, d) below C; labels g, f, a, c | a 0.13(s)<br>b 0.00(s)<br>c 3.33(s)<br>d 3.47(s)<br>e 1.42(d)<br>f 1.83(q)<br>g 5.38(d), 5.58(d) | 5.9<br>3.3<br>3.0<br>5.5<br>2.9<br>1<br>1.6 | 6<br>3<br>3<br>6<br>3<br>1<br>2 |

What is claimed is:

1. A vinylidene silicone compound represented by the general formula

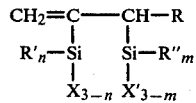

where R is an alkyl group of 1 to 7 carbon atoms or a hydrogen atom; each of R' and R" is an alkyl of 1 to 7 carbon atoms; each of X and X' is a chlorine atom or an alkoxy group of 1 to 4 carbon atoms; and each of n and m is an integer of 0 to 3.

2. A process for preparing a vinyldiene silicone compound represented by the general formula

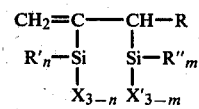

where R is an alkyl group of 1 to 7 carbon atoms or a hydrogen atom; each of R' and R" is an alkyl group of 1 to 7 carbon atoms; each of X and X' is a chlorine atom or an alkoxy group of 1 to 4 carbon atoms; and each of n and m is an integer of 0 to 3, which comprises reacting an alkyl allene represented by the general formula $$\begin{array}{c}H\\ \phantom{x}\diagdown\\ H\end{array}C=C=C\begin{array}{c}H\\ \diagup\\ R\end{array}$$

where R is as defined above, with a disilane represented by the general formula R'$_n$X$_{3-n}$Si$_2$R"$_m$X'$_{3-m}$ where R', R", X, X', n and m are as defined above, in the presence of a phosphine complex of a transition metal.

3. The process according to claim 2, wherein the reaction temperature is from 50° to 200° C.

4. The process according to claim 2, wherein the amount of the phosphine complex of the transition metal is from 0.01 to 5.0 molar % based on the disilane.

* * * * *